(12) United States Patent
Han et al.

(10) Patent No.: US 12,740,967 B2
(45) Date of Patent: Sep. 22, 2026

(54) USE OF ATRACTYLENOLIDE I IN PREPARATION OF MEDICINE FOR PREVENTING AND/OR TREATING CERVICAL CANCER

(71) Applicant: JIANGSU PROVINCE HOSPITAL OF CHINESE MEDICINE, Nanjing (CN)

(72) Inventors: Yue Han, Nanjing (CN); Qingling Ren, Nanjing (CN)

(73) Assignee: JIANGSU PROVINCE HOSPITAL OF CHINESE MEDICINE, Nanjing (CN)

( * ) Notice: Subject to any disclaimer, the term of this patent is extended or adjusted under 35 U.S.C. 154(b) by 96 days.

(21) Appl. No.: 18/838,226

(22) PCT Filed: Nov. 15, 2022

(86) PCT No.: PCT/CN2022/132030
§ 371 (c)(1),
(2) Date: Aug. 13, 2024

(87) PCT Pub. No.: WO2023/160029
PCT Pub. Date: Aug. 31, 2023

(65) Prior Publication Data

US 2025/0114325 A1 Apr. 10, 2025

(30) Foreign Application Priority Data

Feb. 22, 2022 (CN) ......................... 202210163830.0

(51) Int. Cl.
*A61K 31/365* (2006.01)
*A61K 45/06* (2006.01)

(52) U.S. Cl.
CPC ............ *A61K 31/365* (2013.01); *A61K 45/06* (2013.01)

(58) Field of Classification Search
CPC .............................. A61K 31/365; A61K 45/06
See application file for complete search history.

(56) References Cited

FOREIGN PATENT DOCUMENTS

| | | | | |
|---|---|---|---|---|
| CN | 114948938 B | 8/2023 | | |
| WO | WO-2021055705 A1 * | 3/2021 | ........... | C07D 487/22 |
| WO | 2021201680 A1 | 10/2021 | | |

OTHER PUBLICATIONS

Han et al. Purinergic Signalling 2023, 19, 145-153 (published Mar. 2, 2022) (Year: 2022).*
JNJ Abbreviation Meaning (2025). All Acronyms. Retrieved on Mar. 8, 2025 from https://www.allacronyms.com/JNJ. (Year: 2025).*
PubChem Compound Database "JNJ" search results (2025). NIH National Library of Medicine NCBI. Search conducted on Mar. 8, 2025 at https://www.ncbi.nlm.nih.gov/pccompound. (Year: 2025).*
Wang, J. Drug Des. Dev. Ther. 2020, 14, 823-832 (Year: 2020).*
Zhou et al. Chin. J. Exp. Tradit. Med. Formulae 2016, 22, 43-48, partial English translation, translated by USPTO STIC on Jun. 25, 2025. (Year: 2025).*
Han, Yue et al., "P2X7 Receptor Involved in Antitumor Activity of Atractylenolide I in Human Cervical Cancer Cells", Purinergic Signalling, Mar. 2, 2022, pp. 1-9.
Zou, Hui et al.; "Chemical Constituents of Atractylodis Macrocephalae Rhizoma"; Chinese Journal of Experimental Traditional Medical Formulae; vol. 22, No. 17; Sep. 30, 2016; pp. 43-48.
Bhattacharya, Anindya et al.; "Pharmacological characterization of a novel centrally permeable P2X7 receptor antagonist: JNJ-47965567"; British Journal of Pharmacology; vol. 170; Jul. 19, 2013; pp. 624-640.

* cited by examiner

*Primary Examiner* — Svetlana M Ivanova
(74) *Attorney, Agent, or Firm* — NKL Law; Allen Xue

(57) ABSTRACT

A compound represented by formula I, or a salt thereof, or a stereoisomer thereof, or a solvate thereof, or a hydrate thereof can be used in the preparation of a medicine for preventing and/or treating cervical cancer. The compound is preferably atractylenolide I of the combination of atractylenolide I and a P2X7R antagonist can be used in the preparation of a medicine for preventing and/or treating cervical cancer. Meanwhile, for inhibition of the proliferation of SiHa cells, atractylenolide I and the P2X7R antagonist are combined for use to achieve a synergistic effect.

Formula I

7 Claims, 15 Drawing Sheets

USE OF ATRACTYLENOLIDE I IN PREPARATION OF MEDICINE FOR PREVENTING AND/OR TREATING CERVICAL CANCER

FIELD OF THE INVENTION

The present invention belongs to the field of chemical pharmaceuticals, and specifically relates to the use of atractylenolide I in the manufacture of medicaments for the prevention and/or treatment of cervical cancer.

BACKGROUND OF THE INVENTION

Cervical cancer is one of the most-common gynecological malignant tumors, and ranks first among female genital tract tumors. According to global cancer statistics, there were 600 thousand new cases of cervical cancer and 340 thousand deaths in 2020, with an average of one person dying from cervical cancer every 1.5 minutes, showing an upward trend compared to 2018 statistics. In 2020, there was about 110 thousand new cases of cervical cancer and 60 thousand deaths in China, and since 2000, its incidence rate and mortality have been on a young trend year by year. 95% of cervical cancer is caused by human papillomavirus (HPV), and HPV16 and 18 types can be responsible for at least 70% of cervical cancer. Although the promotion and application of HPV vaccines can achieve primary prevention of cervical cancer, due to limitations such as HPV subtypes, age groups, and socio-economic conditions, most cervical cancer patients in clinical practice are diagnosed with stage IB1 or even stage III or IVA. Surgery or radiochemotherapy can damage the immune function of the body and the local vagina, destroy the vaginal microbiota of the body, and easily lead to tumor progression and metastasis, which cannot improve long-term survival rate and affect the prognosis of the disease and the quality of life. Finding new targets or potential medicaments for the treatment of cervical cancer remains a major challenge.

Since proposed by Burnstock in 1972, purinergic signaling has been considered as a promising target for various systemic diseases. In purinergic system, more and more evidences support that purinergic P2X7R plays an important role in different cancers, including lung cancer, colorectal cancer, breast cancer, acute myeloid leukemia, etc. In addition to research on P2X7 ion channels, the development of potential anticancer medicaments targeting purinergic receptors from natural products has also been investigated.

Atractylenolide I (Atr-I) is a natural product extracted from *Atractylodes macrocephala*, a traditional Chinese medicine. In previous studies, Atr-I was found to be sensitive to human colorectal cancer cells, ovarian cancer cells, breast cancer cells, gastric cancer cells and bladder cancer cells. However, due to the different pathogenesis and treatment methods of different cancers, it is unclear whether Atr-I has anti-tumor activity against cervical cancer and whether it can be used for the treatment of human cervical cancer, and no relevant reports is found.

Atractylenolide I

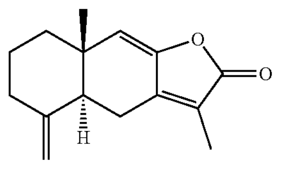

SUMMARY OF THE INVENTION

The object of the present invention is to provide the use of Atr-I in the manufacture of medicaments for the prevention and/or treatment of cervical cancer.

The present invention provides the use of a compound represented by formula I, or a salt thereof, or a stereoisomer thereof, or a solvate thereof, or a hydrate thereof in the manufacture of medicaments for the prevention and/or treatment of cervical cancer:

Formula I

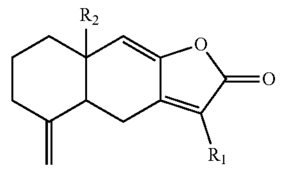

wherein, $R_1$ and $R_2$ are each independently selected from the group consisting of H, $C_1$-$C_6$ alkyl, halogen, carboxyl, hydroxyl, and amino.

Further, the compound is represented by formula II:

Formula II

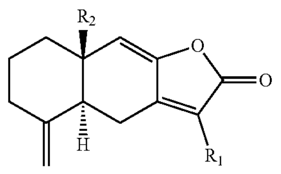

wherein, $R_1$ and $R_2$ are each independently selected from the group consisting of H, $C_1$-$C_6$ alkyl, halogen, carboxyl, hydroxyl, and amino.

Further, the compound is Atr-I, with the following structure:

Atractylenolide I

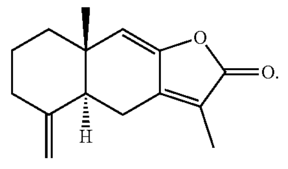

Further, the cervical cancer is that caused by HPV16 and/or HPV18.

Further, the medicament is that inhibiting the proliferation of Hela cells and/or SiHa cells; and/or, the medicament is that inhibiting the clone of Hela cells and/or SiHa cells; and/or, the medicament is that promoting the damage of the plasma membrane to release LDH.

Further, the medicament is that inhibiting the expression of P2X7 receptor protein.

The present invention also provides a pharmaceutical composition for the prevention and/or treatment of cervical cancer, which is composed of the above compound, or a salt thereof, or a stereoisomer thereof, or a solvate thereof, or a hydrate thereof, and a P2X7R antagonist; preferably, the molar ratio of the above compound, or a salt thereof, or a stereoisomer thereof, or a solvate thereof, or a hydrate thereof to a P2X7R antagonist is (1-10):1;

more preferably, the molar ratio of the above compound, or a salt thereof, or a stereoisomer thereof, or a solvate thereof, or a hydrate thereof to a P2X7R antagonist is (2-4):1.

The present invention also provides the use of the pharmaceutical composition mentioned above in the manufacture of medicaments for the prevention and/or treatment of cervical cancer;

preferably, the cervical cancer is that caused by HPV16;

more preferably, the medicament is that inhibiting the proliferation of SiHa cells; and/or, the medicament is that inhibiting the clone of SiHa cells; and/or, the medicament is that promoting the damage of the plasma membrane to release LDH; and/or, the medicament is that inhibiting the expression of P2X7 receptor protein.

The present invention also provides that the above compound, or a salt thereof, or a stereoisomer thereof, or a solvate thereof, or a hydrate thereof in combination with a P2X7R antagonist is used in the manufacture of medicaments for the prevention and/or treatment of cervical cancer;

preferably, the molar ratio of the above compound, or a salt thereof, or a stereoisomer thereof, or a solvate thereof, or a hydrate thereof to a P2X7R antagonist is (1-10):1;

and/or, the cervical cancer is that caused by HPV16;

more preferably, the molar ratio of the above compound, or a salt thereof, or a stereoisomer thereof, or a solvate thereof, or a hydrate thereof to a P2X7R antagonist is (2-4):1;

and/or, the medicament is that inhibiting the proliferation of SiHa cells; and/or, the medicament is that inhibiting the clone of SiHa cells; and/or, the medicament is that promoting the damage of the plasma membrane to release LDH; and/or, the medicament is that inhibiting the expression of P2X7 receptor protein.

The present invention also provides a medicament for the prevention and/or treatment of cervical cancer, which is a preparation prepared from the above compound, or a salt thereof, or a stereoisomer thereof, or a solvate thereof, or a hydrate thereof, or the above pharmaceutical composition as the active ingredient, in combination with pharmaceutically acceptable excipients or auxiliary ingredients.

Compared with the prior art, the beneficial effects of the present invention are:

The research in the present invention indicates that Atr-I has a significant inhibitory effect on the proliferation of human cervical cancer cells, and thus Atr-I can be used in the manufacture of medicaments for the prevention and/or treatment of cervical cancer. Moreover, the combination of Atr-I and a P2X7R antagonist can play a synergistic effect on the inhibition of SiHa cell proliferation, which can have better actions for the prevention and/or treatment of cervical cancer.

Obviously, based on the above content of the present invention, according to the common technical knowledge and the conventional means in the field, other various modifications, alternations, or changes can further be made, without department from the above basic technical spirits.

With reference to the following specific examples, the above content of the present invention is further illustrated. But it should not be construed that the scope of the above subject matter of the present invention is limited to the following examples. The techniques realized based on the above content of the present invention are all within the scope of the present invention.

EXAMPLES

Figure 1:
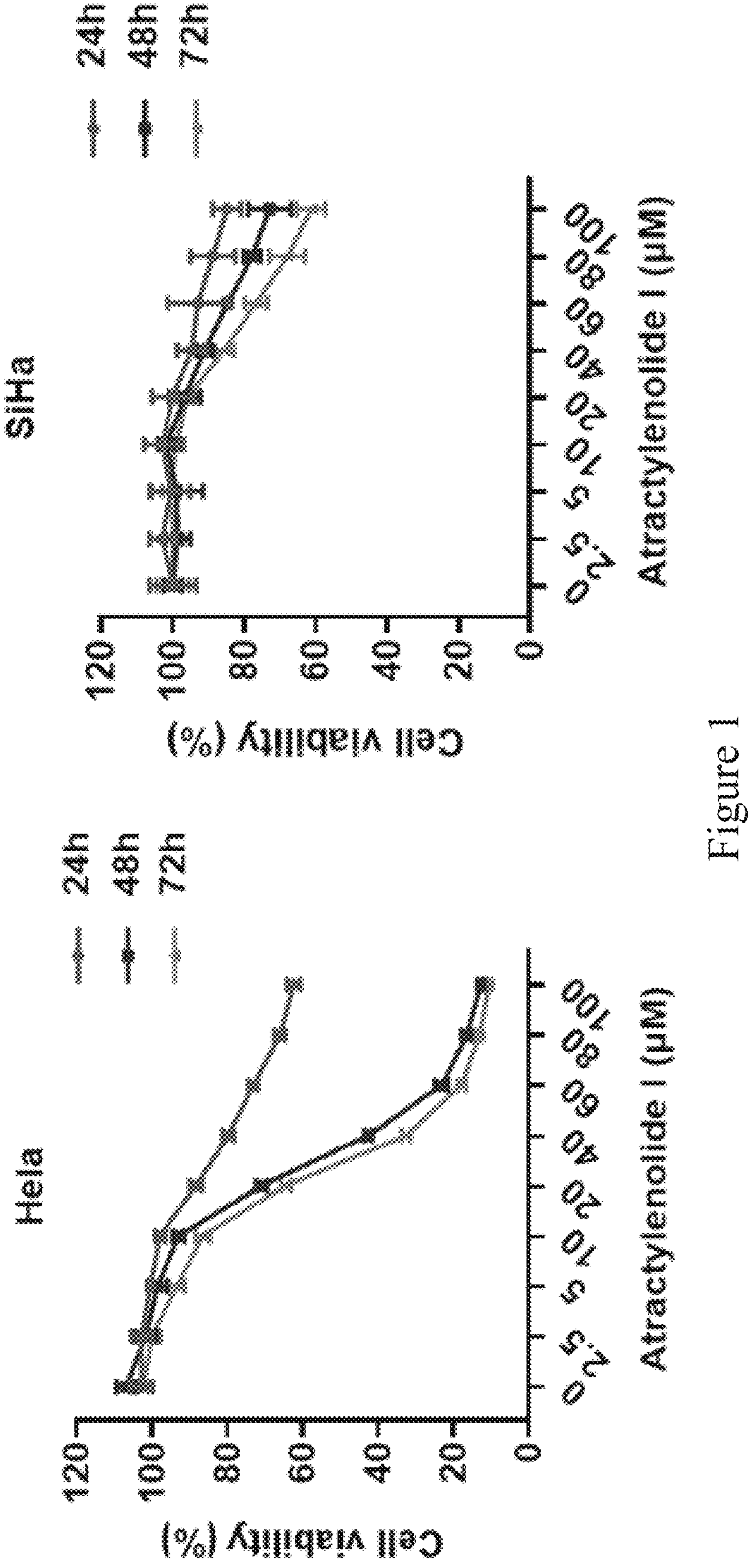
FIG. 1. Effects of Atr-I on the proliferation of Hela cells and SiHa cells.

Unless otherwise specified, the raw materials and equipment used in the specific examples of the present invention are known products obtained by purchasing those commercially available.

Example 1. Study on the Inhibitory Effect of Atr-I on Cervical Cancer Cells

I. Experimental Methods

The cell lines selected were human cervical cancer Hela (HPV18+) and Siha (HPV16+) cell lines.

Experimental drugs: Atractylenolide I, LPS (100 ng/ml), P2X7R agonist BzATP, P2X7R antagonist JNJ.

1. Cell Proliferation Experiment

Assay of cell viability by CCK-8 kit: Cells (cell density: 1000 cells/well) were inoculated in a 96-well plate and cultured for 24 hours. After adhering to the wall, the cells were stimulated for different times (24 h, 48 h, 72 h) using varied concentrations of Atr-I (0, 2.5, 5, 10, 20, 40, 60, 80, 100, 160 μM), P2X7R agonist BzATP (0, 10, 100, 1000 μM), and P2X7R antagonist JNJ (0, 2.5, 5, 10, 20, 40, 80, 100, 1000 μM), respectively, while the cells were stimulated with Atr-I 40 μM+BzATP 100 μM, Atr-I 80 μM+BzATP 100 μM, Atr-I 40 μM+JNJ 20 μM, Atr-I 80 μM+JNJ 20 μM for 24 h, 48 h, or 72 h, respectively. Cell proliferation was detected using Cell Counting Kit-8 (CCK-8). Based on the above experimental results, the optimal inhibition concentrations of Atr-I, JNJ, and BzATP against cell proliferation were calculated.

2. Cytotoxicity Assay (Lactate Dehydrogenase (LDH) Release Assay)

Cells were cultured in a 96-well plate (cell density: 1000 cells/well) for 24 h, 48 h, and 72 h, respectively. Based on the experimental results of the "cell proliferation experiment", the cells were cultured respectively with 40 μM Atr-I, 80 μM Atr-I, JNJ 20 μM, BzATP 100 μM, Atr-I 40 μM+BzATP 100 μM, Atr-I 80 μM+BzATP 100 μM, Atr-I 40 μM+JNJ 20 μM, Atr-I 80 μM+JNJ 20 μM for 24 h, 48 h, and 72 h, and then the supernatant of cell culture was transferred to a new 96-well plate for LDH analysis. The LDH detection kit (Beyotime Biotechnology, Shanghai, China) was used to detect the cytotoxicity.

3. Cell Cycle Assay

The proportion of apoptotic cells was measured using the Annexin V-AF647/PI Apoptosis Kit (E-CK-A213; Elabscience Biotechnology, Wuhan, China). The cells in logarithmic growth phase were used and seeded in a culture bottle at a suspension density of $1\times10^6$ cells/mL, and then cultured in a $CO_2$ incubator for 24 h. The cells were stimulated by adding Atr-I 40 μM+BzATP 100 μM, Atr-I 80 μM+BzATP 100 μM, Atr-I 40 μM+JNJ 20 μM, Atr-I 80 μM+JNJ 20 μM, Atr-I 40 μM, and Atr-I 80 μM, respectively, and then cultured for 48 h, followed by washing twice with PBS. Subsequently, the cells were re-suspended in 500 μL of the binding buffer. After adding 5 μL of Annexin V-AF647 and 5 μL of PI to the cell suspension, respectively, the cell cycle was assayed using FACSCalibur flow cytometry (BD Biosciences, San Jose, CA, USA). The data were analyzed with FlowJo software (FlowJo, Ashland, OR, USA).

4. Cell Cloning Experiment

SiHa cells and Hela cells were seeded into culture flasks at a suspension density of $1\times10^5$ cells/mL, respectively, and incubated in a $CO_2$ incubator for 48 h. Cells were seeded into Petri dishes at a density of 100 cells/ml, treated with Atr-I at different concentrations (0 M, 20 M, 40 μM, 80 μM), and then stained with 0.1% crystal violet solution to calculate the survival rate of cell clone.

5. Determining the Expression of P2X7 by Western Blot Assay

Proteins from Hela and SiHa cell culture media treated with Atr-I (0 μM, 20 μM, 40 μM, 80 μM) for 48 h were extracted with RIPA cell lysis buffer, and the protein concentration was determined by BCA assay kit. Protein samples and the detection reagent buffer were added, denatured by heating under boiling, subjected to electrophoresis and transferring to membrane, and blocked with 5% skim milk powder for 1 h. Then, the primary antibody was added and incubated overnight at 4° C., followed by washing thrice with 1*TBST. Subsequently, the protein was allowed to incubate together with the secondary antibody at 37° C. for 1 h, to which was added ECL detection solution for exposure imaging.

II. Experimental Results

1. Experiment Results for Cell Proliferation

Figure 2:
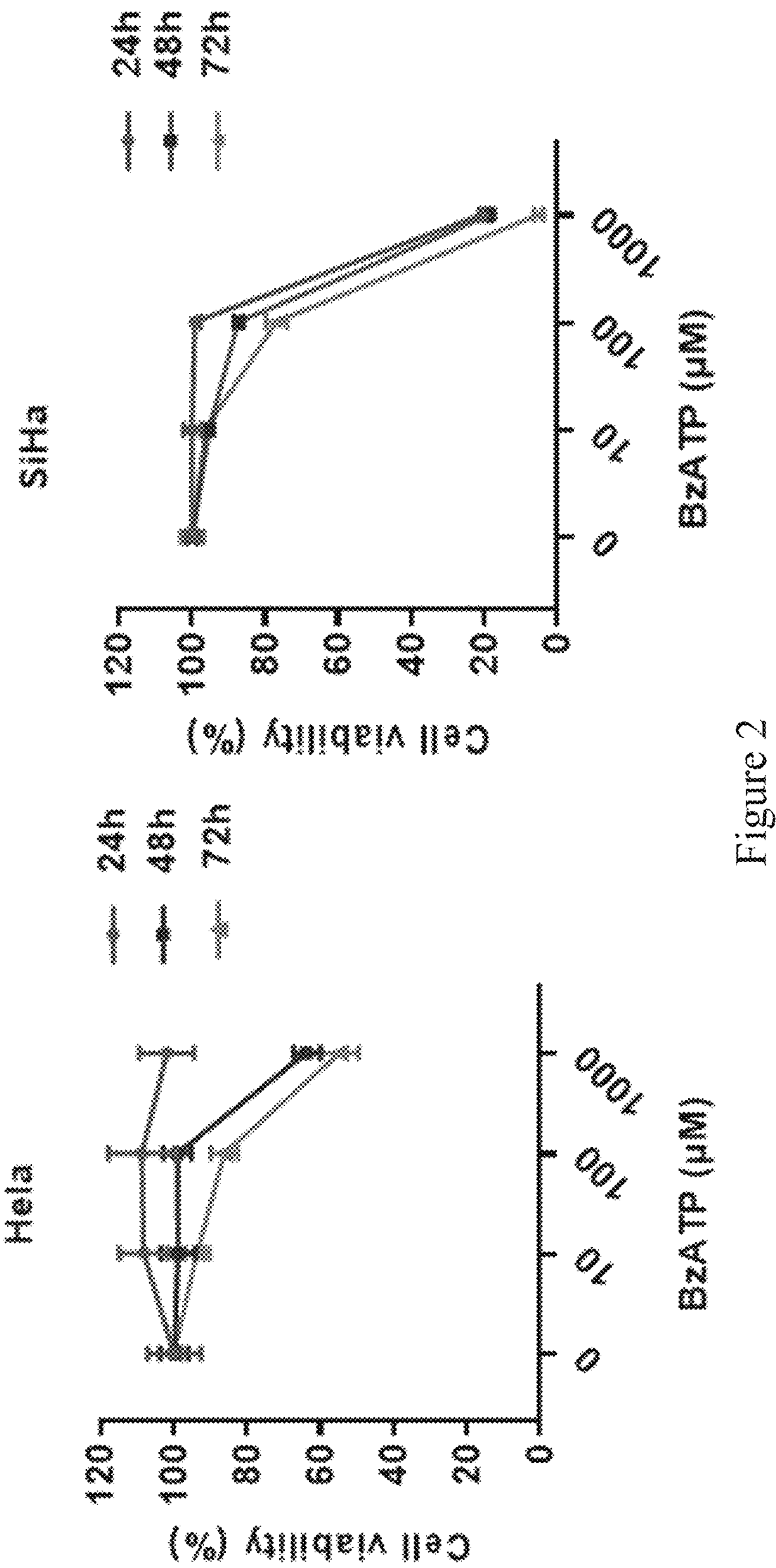
FIG. 2. Effects of BzATP on the proliferation of Hela cells and SiHa cells.
Figure 3:
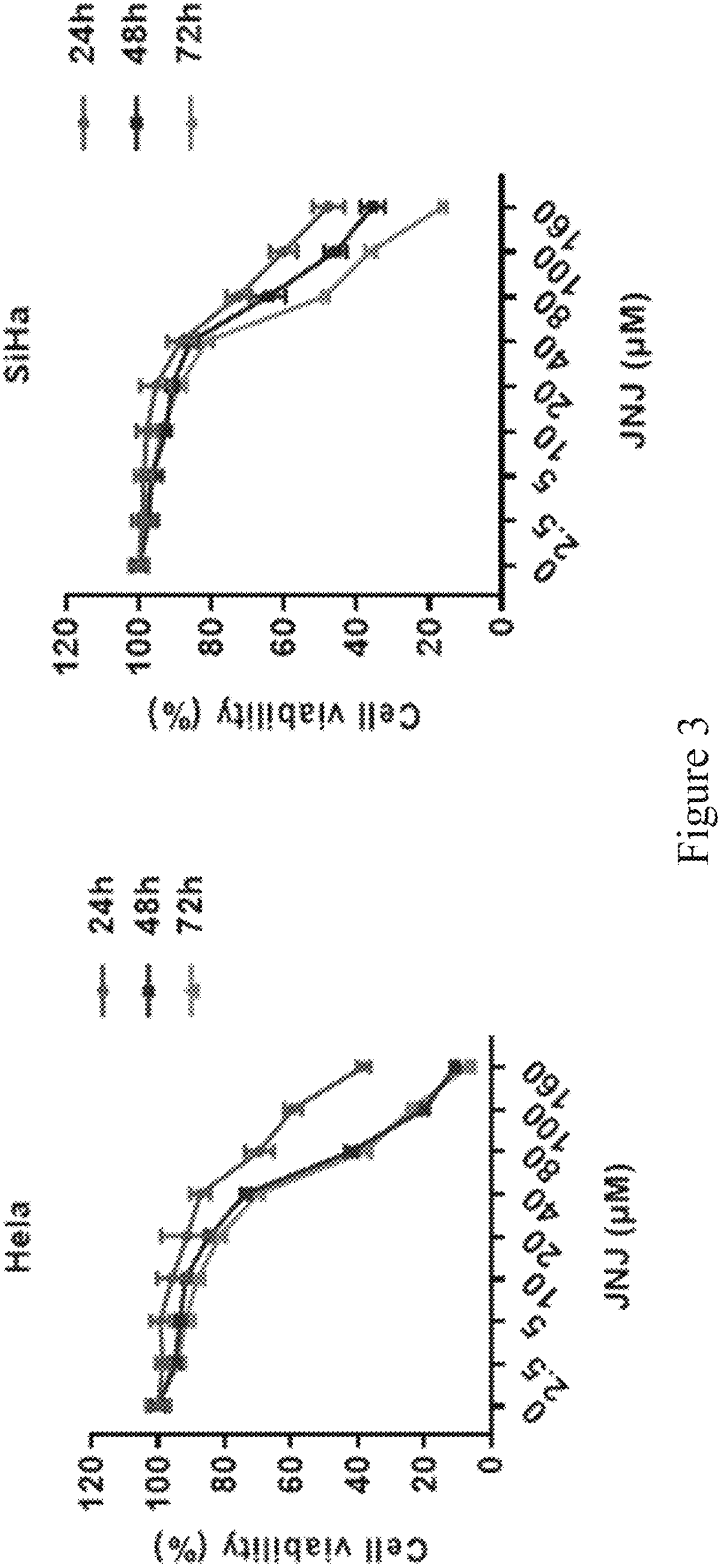
FIG. 3. Effects of JNJ on the proliferation of Hela cells and SiHa cells.

The CCK8 assay results in FIGS. 1-3 showed that Atr-I significantly inhibited the growth of Hela cells and SiHa cells in a dose and time-dependent manner, in which Hela cells were highly sensitive to Atr-I, while SiHa cells showed higher tolerance to Atr-I, and thus Atr-I had a significantly better inhibitory effect on Hela cells than SiHa cells. BzATP and JNJ also significantly inhibited the growth of Hela cells and SiHa cells in a dose and time-dependent manner, wherein SiHa cells were more sensitive to BzATP compared to Hela cells, but Hela cells and SiHa cells are both sensitive to JNJ. The optimal inhibitory concentrations of Atr-I are 40 μM against Hela cells, and 80 μM against SiHa cells.

Figure 4:
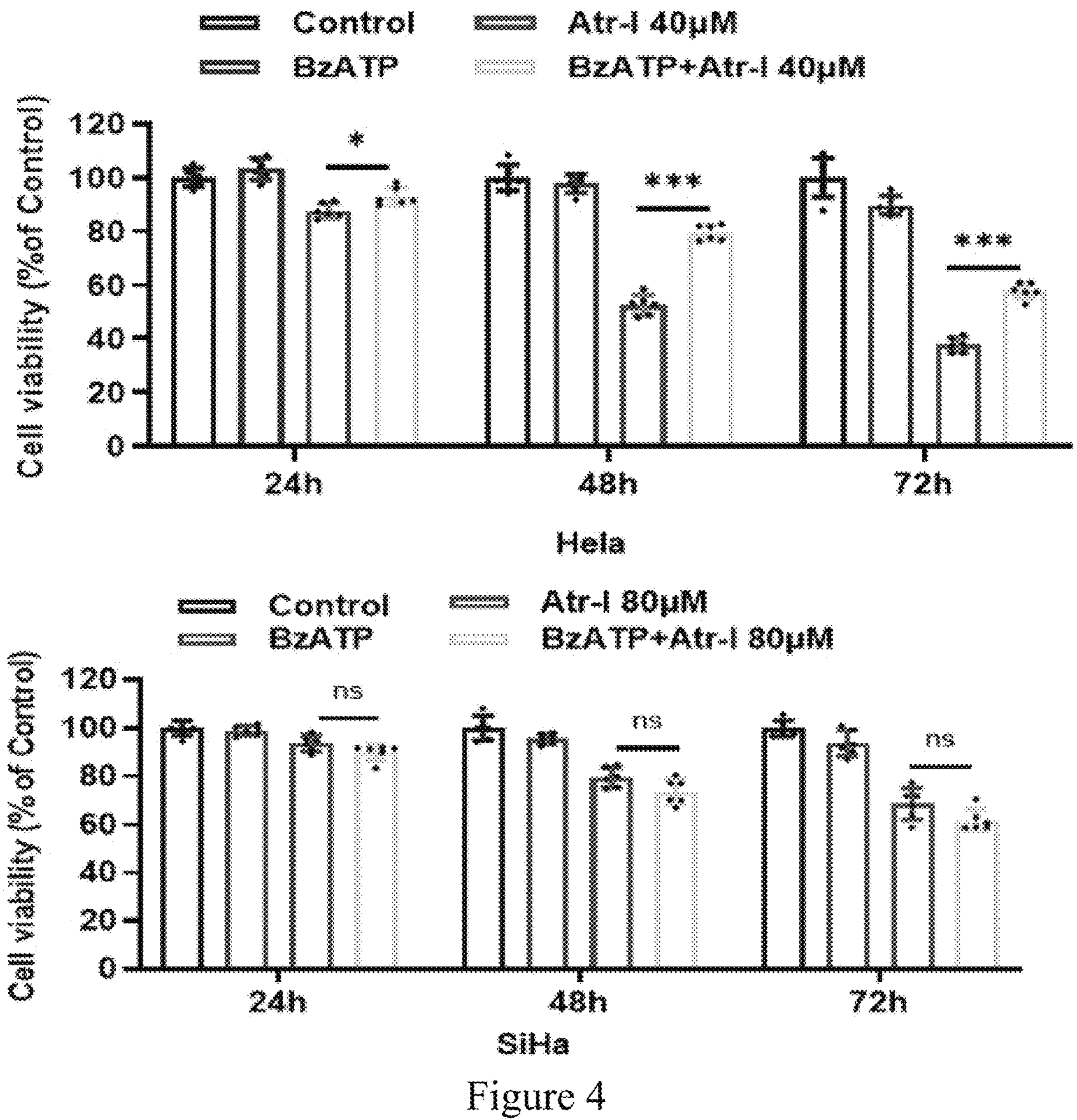
FIG. 4. Effects of Atr-I in combination with BzATP on the proliferation of Hela cells and SiHa cells.

As shown in FIG. 4, after Hela cells were treated with Atr-I 40 μM and Atr-I 40 μM+BzATP 100 μM, and SiHa cells were treated with Atr-I 80 μM and Atr-I 80 μM+BzATP 100 μM, the results indicated that for Hela cells, the combination of BzATP and Atr-I not only failed to enhance the inhibitory effect of Atr-I on Hela cell viability, but also weakened the inhibitory effect of Atr-I on Hela cell viability; for SiHa cells, the combination of BzATP and Atr-I could not improve the inhibitory effect of Atr-I on SiHa cell viability yet. The experimental results demonstrated that the combination of P2X7R agonist BzATP and Atr-I did not have a synergistic effect on inhibiting the growth of cervical cancer cells, but rather had an antagonistic effect on inhibiting Hela cell growth. It could be found that the combination of a P2X7R agonist and Atr-I is not conducive to the prevention and/or treatment of cervical cancer.

Figure 5:
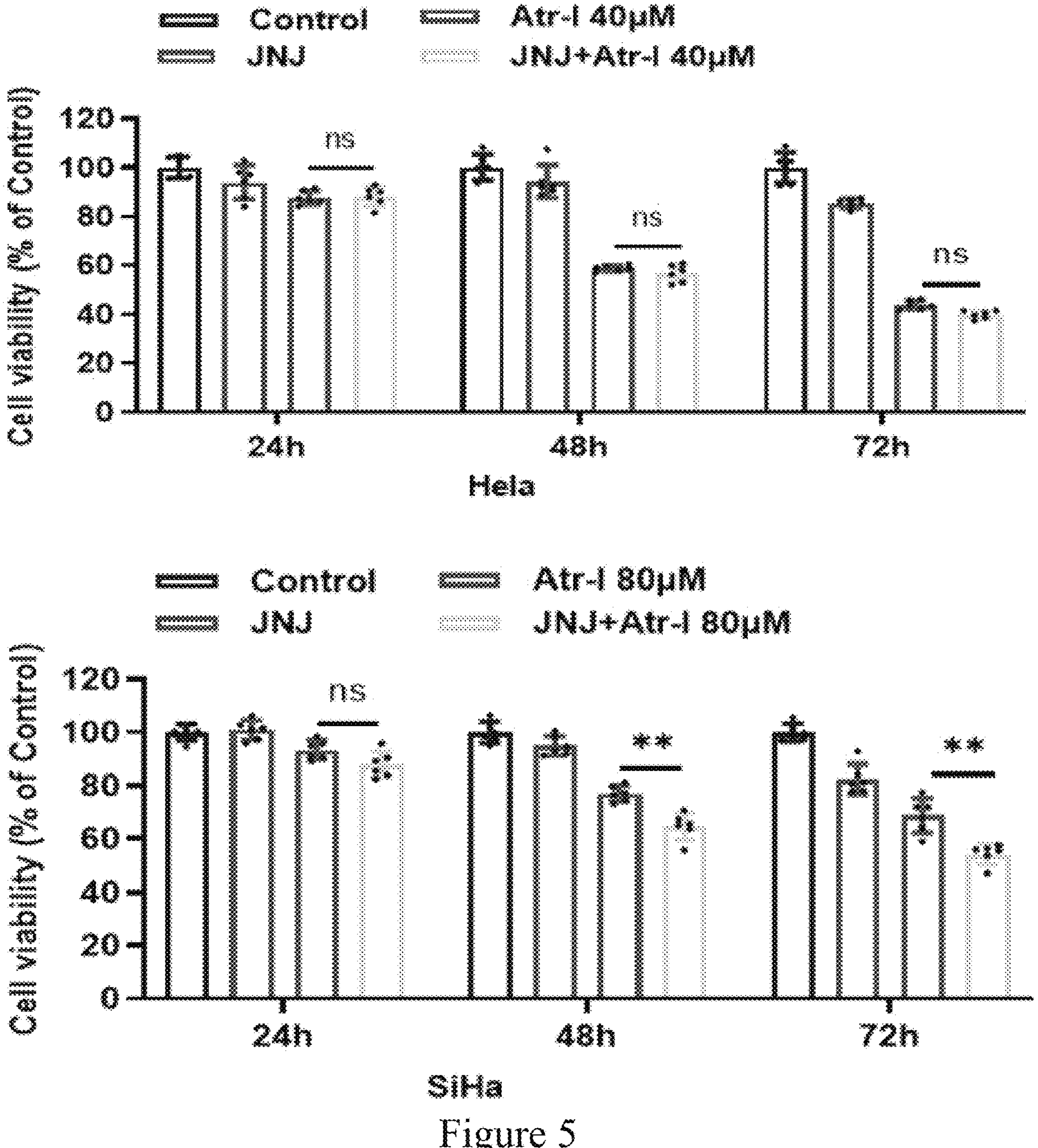
FIG. 5. Effects of Atr-I in combination with JNJ on the proliferation of Hela cells and SiHa cells.

As shown in FIG. 5, after Hela cells were treated with Atr-I 40 μM and Atr-I 40 μM+JNJ 20 μM, and SiHa cells were treated with Atr-I 80 μM and Atr-I 80 μM+JNJ 20 μM, the results indicated that for Hela cells, the combination of JNJ and Atr-I failed to enhance the inhibitory effect of Atr-I on Hela cell viability; for SiHa cells, the combination of JNJ and Atr-I could improve the inhibitory effect of Atr-I on SiHa cell viability. The experimental results suggested that the combination of P2X7R antagonist JNJ and Atr-I had a synergistic effect on inhibiting the growth of cervical cancer SiHa cells. The combination of a P2X7R antagonist and Atr-I was expected to have reinforcing effectiveness for the prevention and/or treatment of cervical cancer.

2. Experimental Results of Cell Clonal Proliferation

Figures 6, 7:
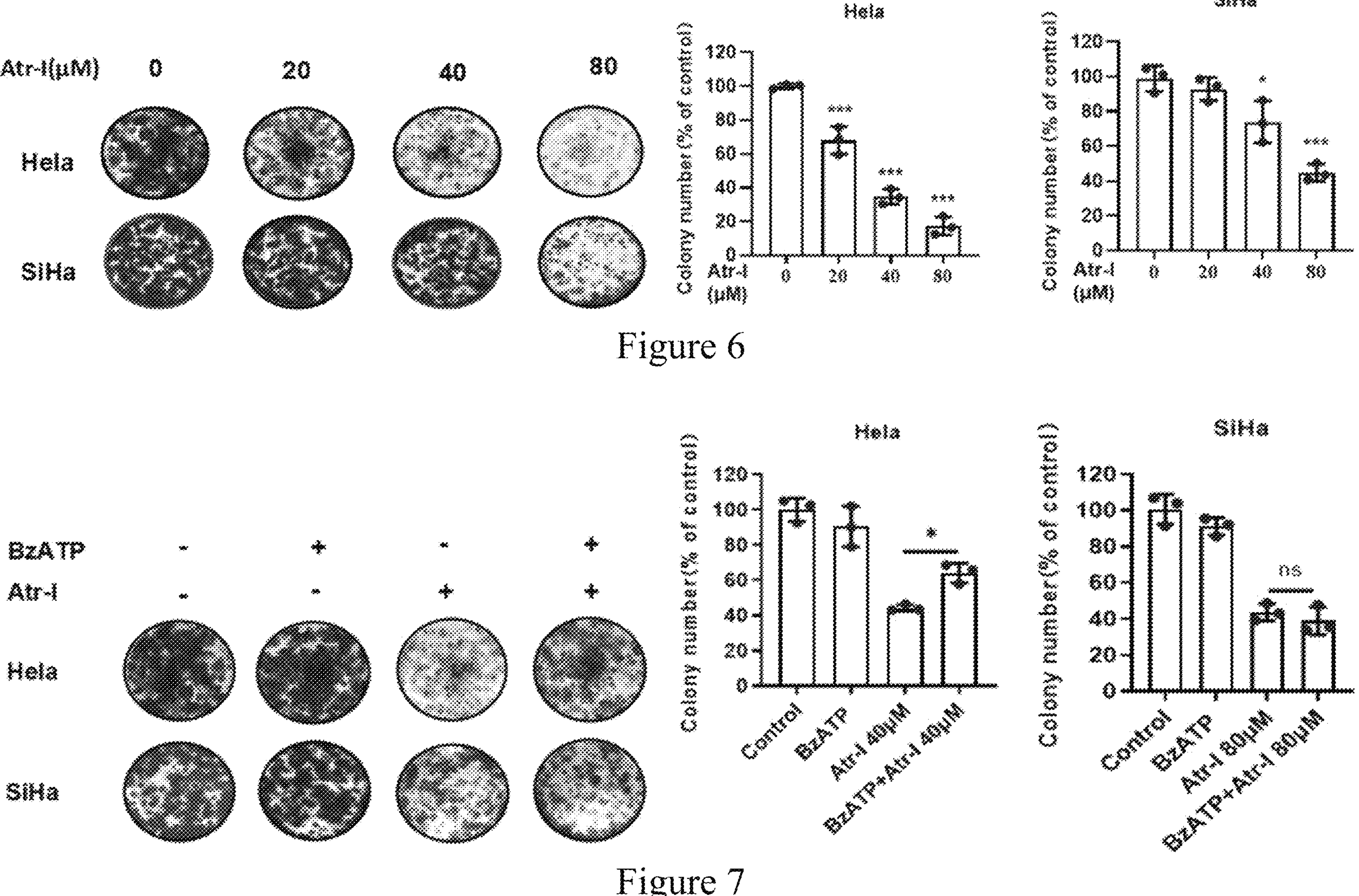
FIG. 6. Effects of Atr-I on the clone of Hela cells and SiHa cells.
FIG. 7. Effects of Atr-I in combination with BzATP on the clone of Hela cells and SiHa cells.
Figure 8:
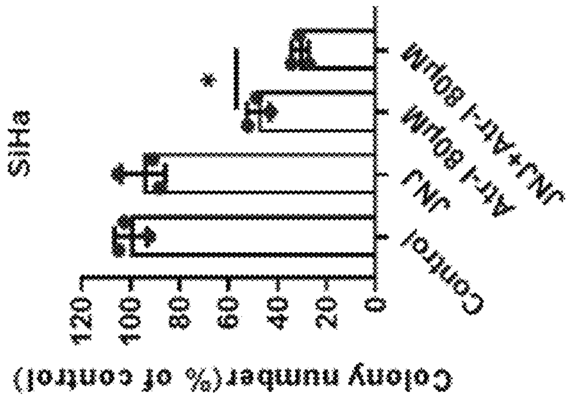
FIG. 8. Effects of Atr-I in combination with JNJ on the clone of Hela cells and SiHa cells.
Figure 8:
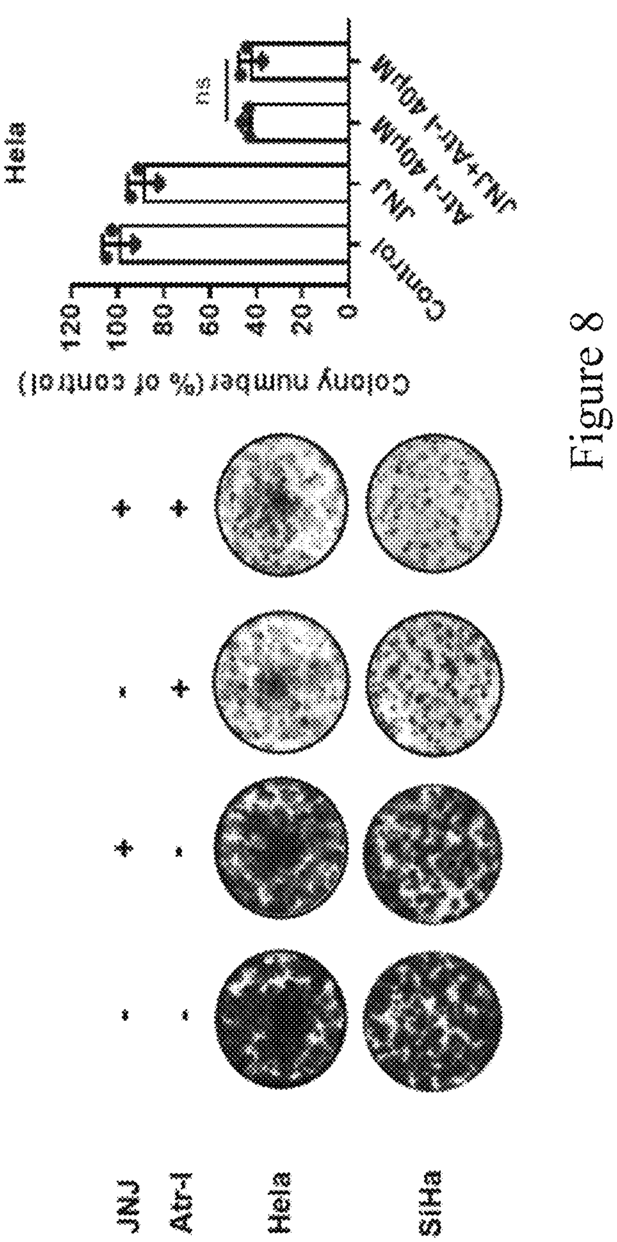

After treating both cell lines with Atr-I, compared to SiHa cells, Atr-I was more effective in inhibiting the clonal proliferation of Hela cells (FIG. 6). After treating Hela cells and SiHa cells with Atr-I+BzATP 100 μM respectively, it was found that the combination of Atr-I and BzATP not only did not significantly inhibit the clonal proliferation of Hela cells and SiHa cells, but also promoted the clonal proliferation of Hela cells compared to using Atr-I alone (FIG. 7). After treating Hela cells and SiHa cells with the combination of Atr-I and JNJ, respectively, it was found that the combination could more significantly inhibit the clonal proliferation of SiHa cells (FIG. 8). The results were consistent with the previous findings, indicating that Atr-I could inhibit the proliferation of Hela cells and SiHa cells. Moreover, the combination of Atr-I and JNJ had a synergistic effect on inhibiting SiHa cell proliferation.

3. Results of LDH Release Assay

Figure 9:
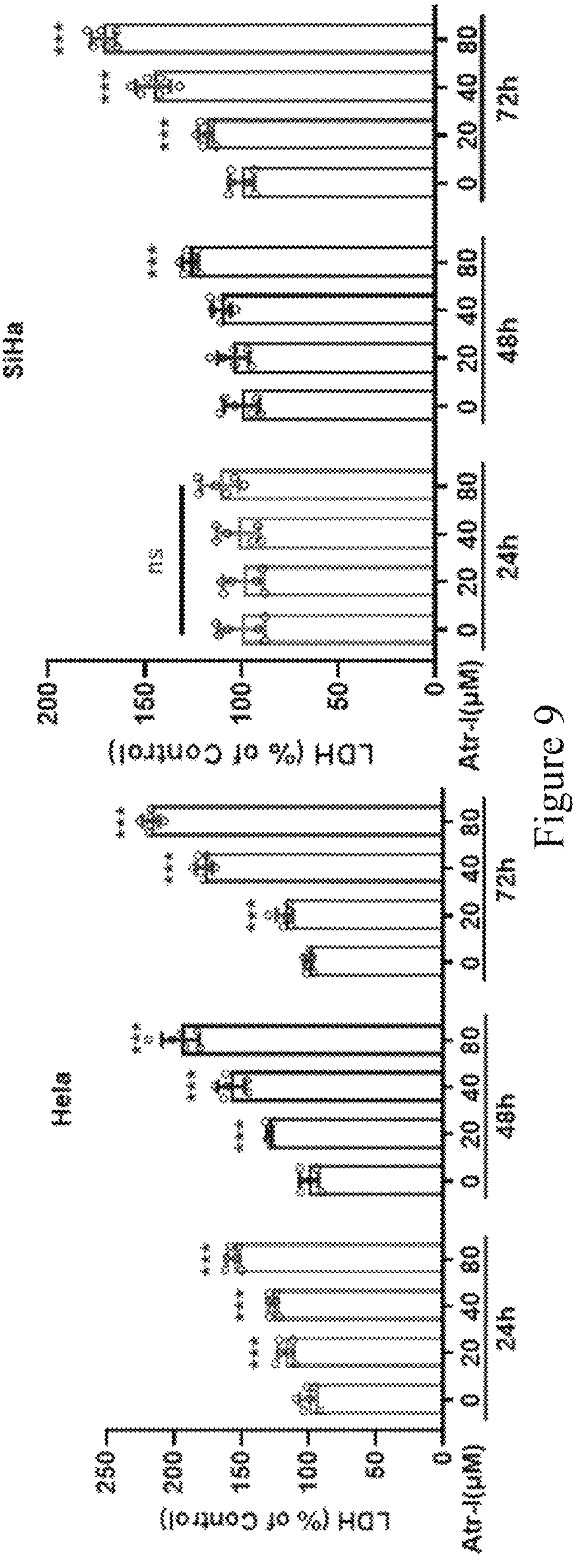
FIG. 9. Effects of Atr-I on the LDH release from Hela cells and SiHa cells.
Figure 10:
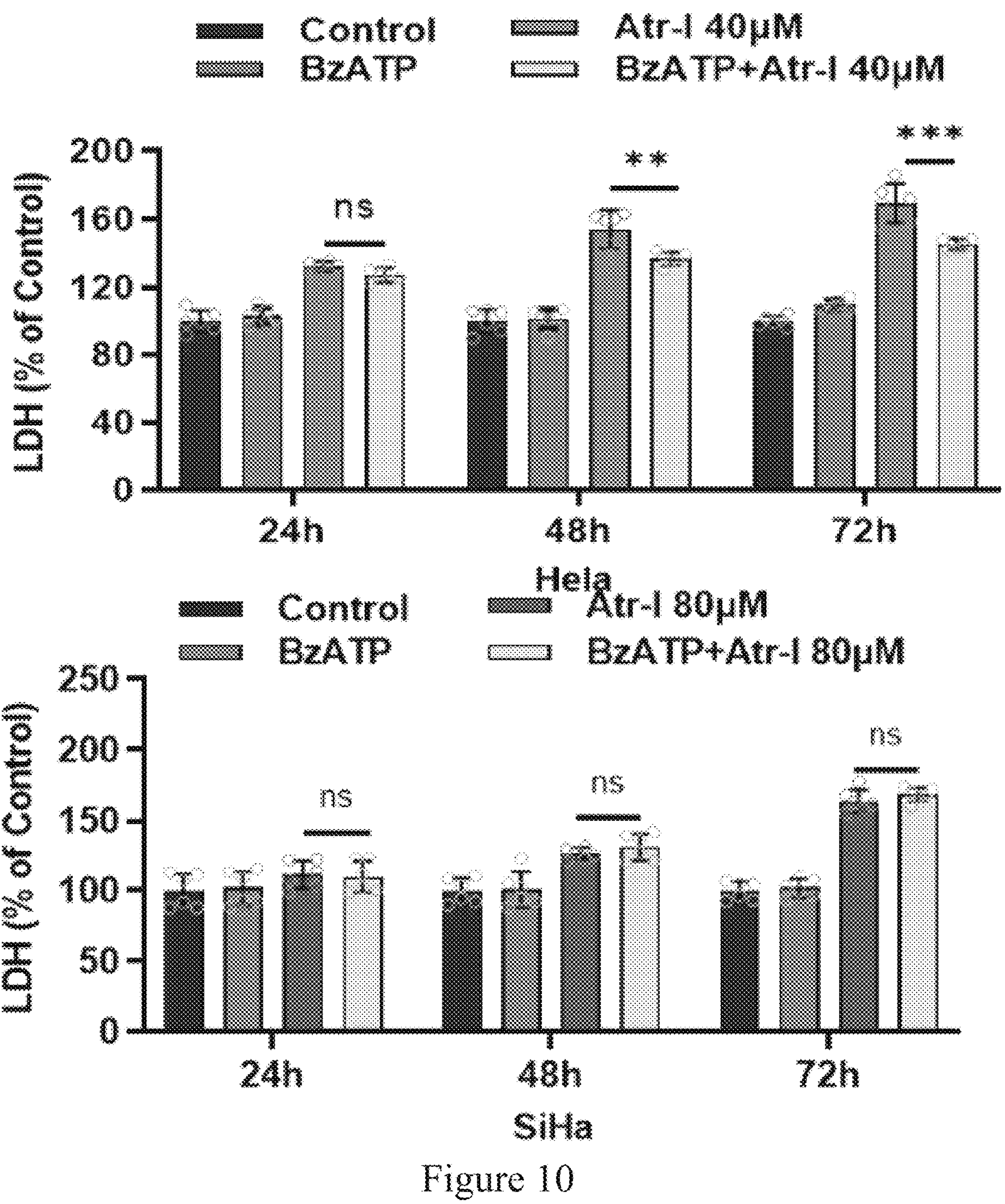
FIG. 10. Effects of Atr-I in combination with BzATP on the LDH release from Hela cells and SiHa cells.
Figure 11:
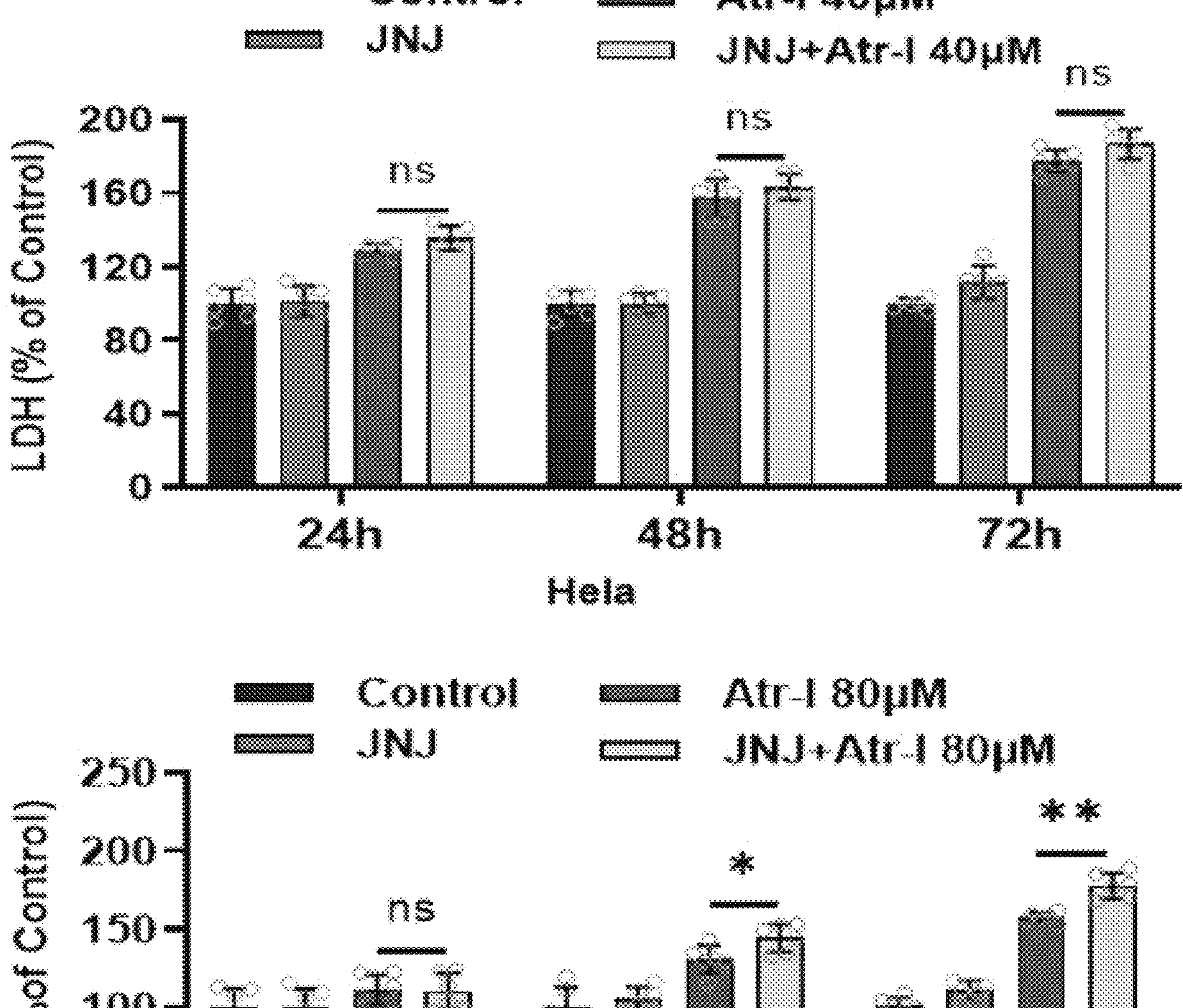
FIG. 11. Effects of Atr-I in combination with JNJ on the LDH release from Hela cells and SiHa cells.

It was found that Atr-I could damage the integrity of the cytoplasmic membranes of Hela and SiHa cells, and promote LDH release, that were the most significant 72 h after treatment (FIG. 9). Once Hela and SiHa cells were treated with the combination of Atr-I and BzATP, LDH release was significantly inhibited (FIG. 10); after SiHa cells were treated with the combination of Atr-I and JNJ, a significant increase in LDH release was shown after 48 h (FIG. 11).

4. Results of Cell Cycle Assay

Figure 12:
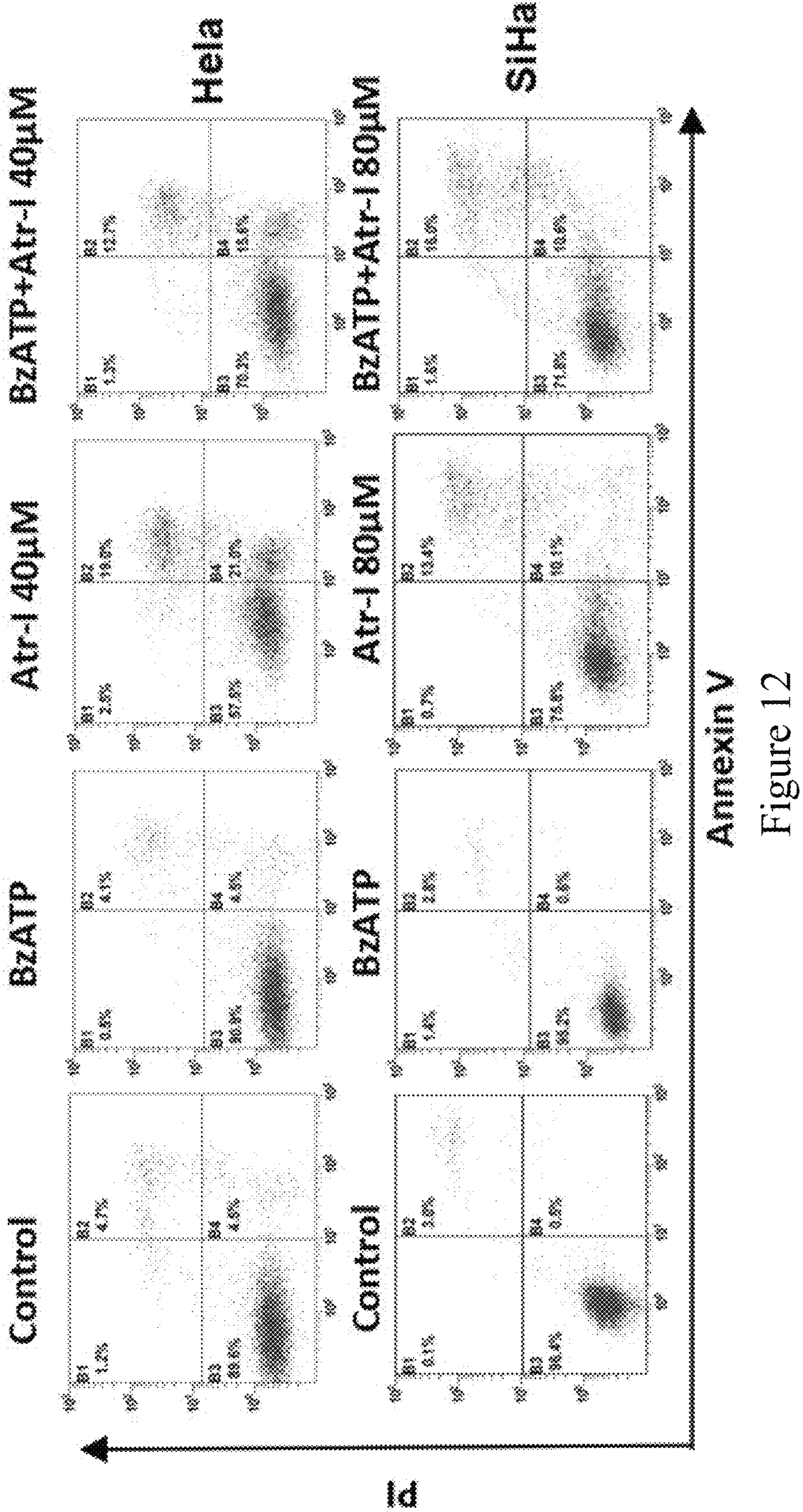
FIG. 12. Flow cytometry assay results of Hela cells and SiHa cells treated with Atr-I+BzATP, respectively.
Figure 13:
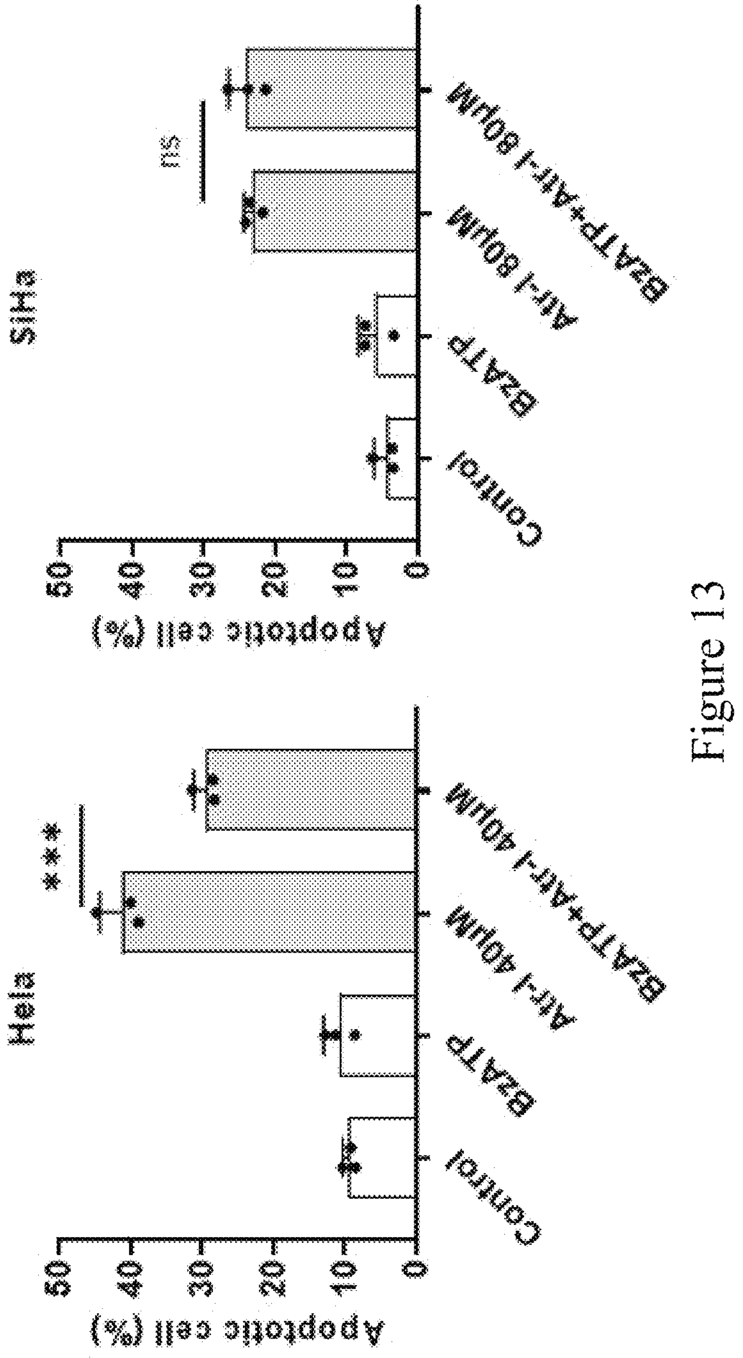
FIG. 13. Statistical results of apoptosis in Hela cells and SiHa cells treated with Atr-I+BzATP, respectively.

The results of flow cytometry showed that BzATP inhibited Atr-I-induced apoptosis in Hela cells, but had no effect on Atr-I-induced apoptosis in SiHa cells (FIGS. 12 and 13).

Figure 14:
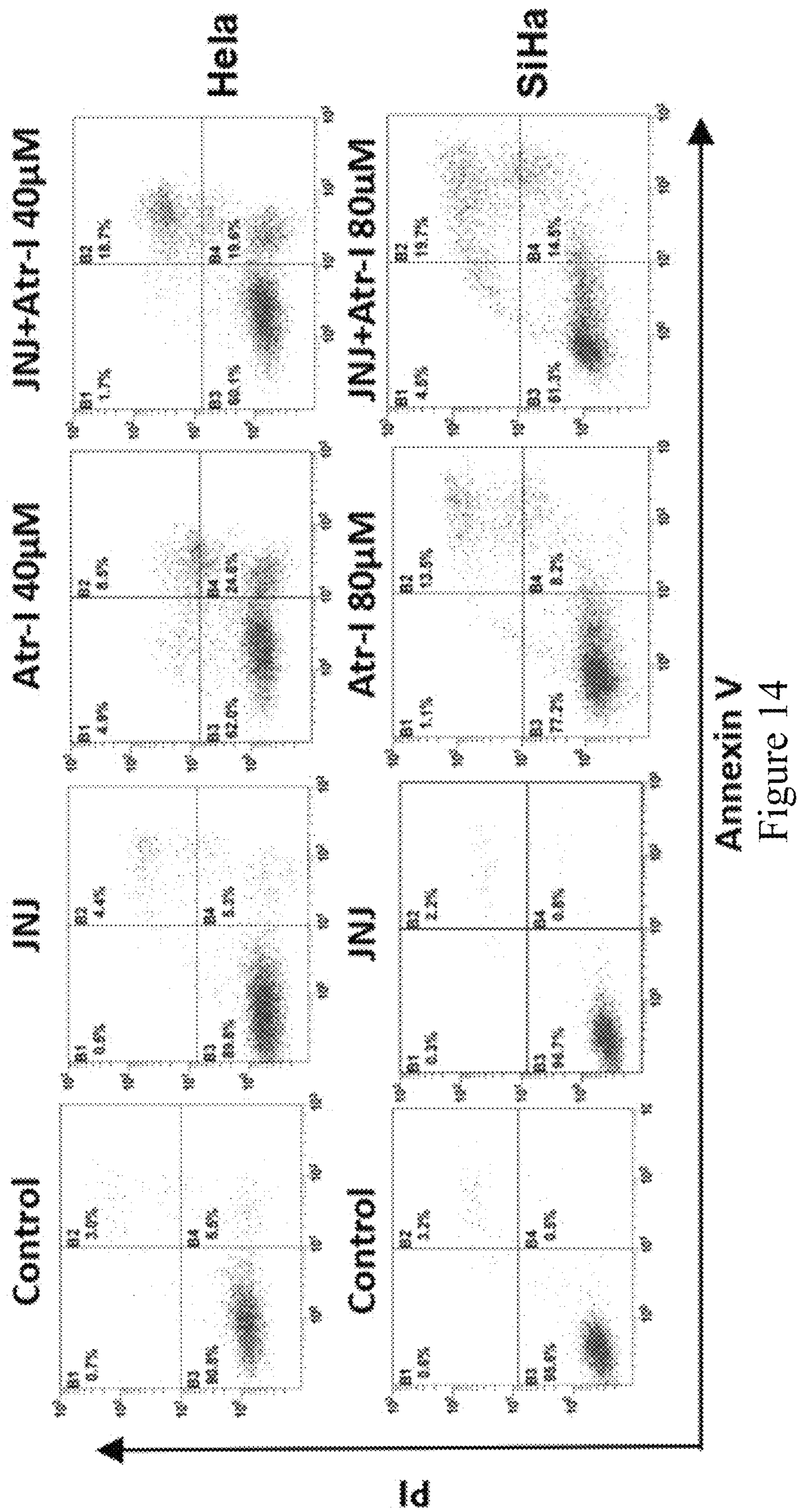
FIG. 14. Flow cytometry assay results of Hela cells and SiHa cells treated with Atr-I+JNJ, respectively.
Figure 15:
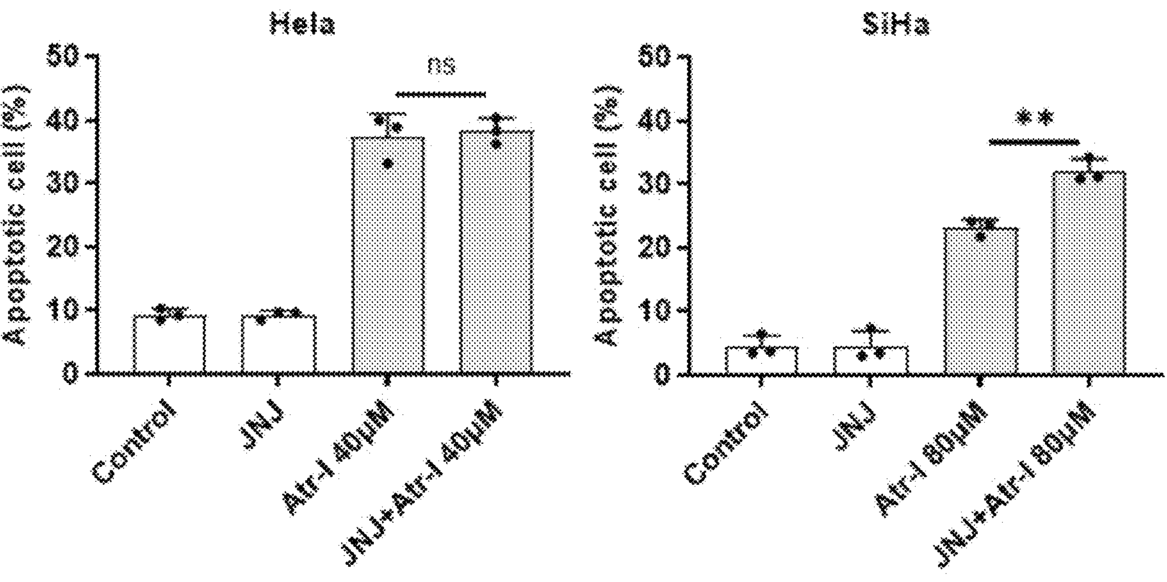
FIG. 15. Statistical results of apoptosis in Hela cells and SiHa cells treated with Atr-I+JNJ, respectively.
Figure 16:
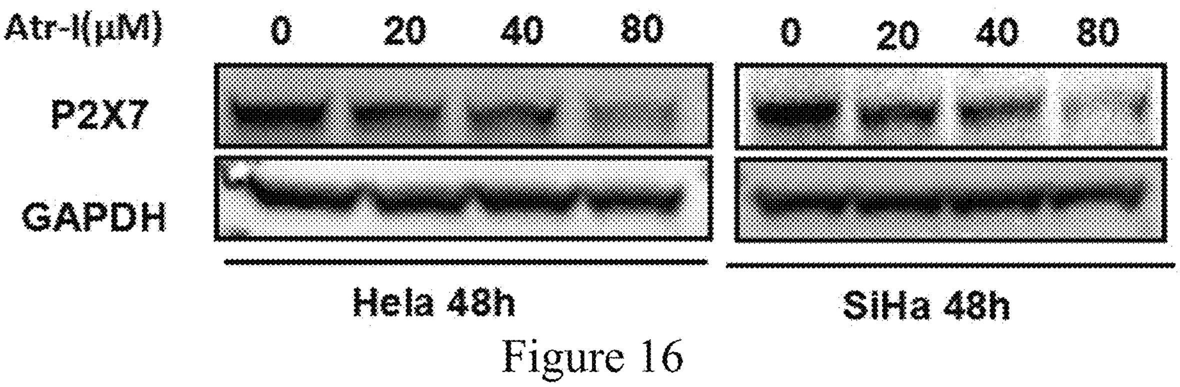
FIG. 16. Western blot assay on the expression of P2X7 protein in Hela cells treated with Atr-I.
Figure 17:
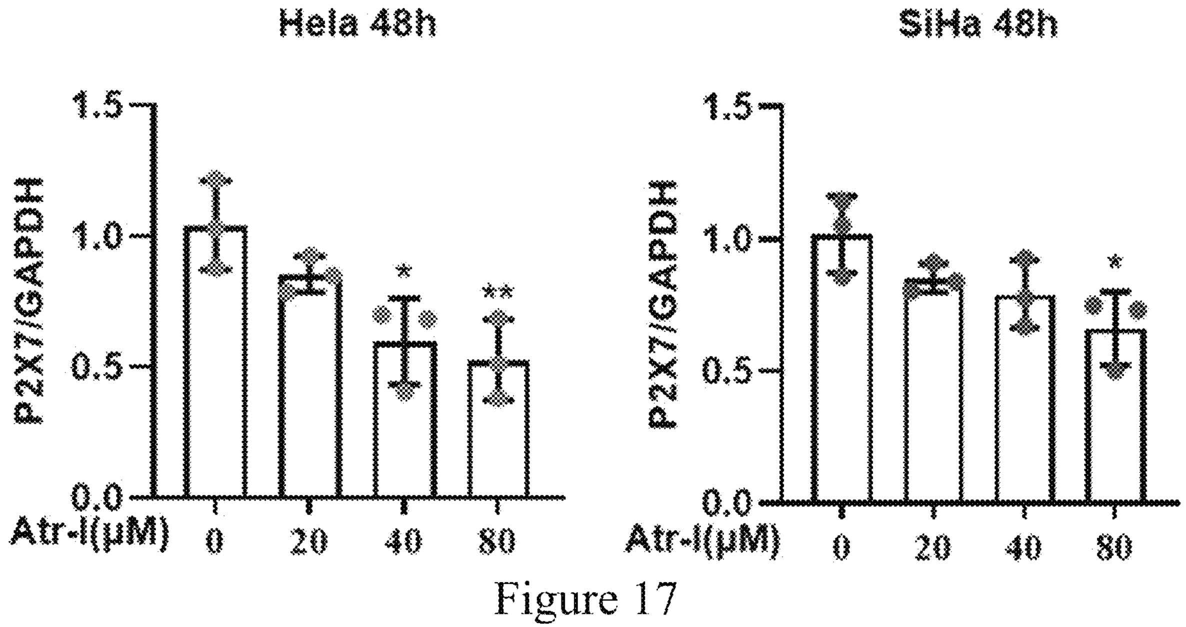
FIG. 17. Western blot assay on the expression of P2X7 protein in SiHA cells treated with Atr-I.

JNJ could promote the apoptosis of SiHa cells induced by Atr-I, but has no effect on the apoptosis of Hela cells induced by Atr-I (FIGS. 14 and 15).

5. Results of P2X7 Expression by WB Assay

Reduced expression of P2X7 receptor protein was observed in Hela cells and SiHa cells treated with Atr-I, demonstrating that P2X7 receptor was involved in the inhibition of Atr-I against the viability of cervical cancer cells.

In summary, the research results of the present invention indicated that Atr-I had a significant inhibitory effect on the proliferation of human cervical cancer cells, and thus Atr-I might be used in the manufacture of medicaments for the prevention and/or treatment of cervical cancer. Moreover, for inhibiting the proliferation of SiHa cells, the combination of Atr-I and P2X7R antagonists could have a synergistic effect, and play better actions for the prevention and/or treatment of cervical cancer.

The invention claimed is:

1. A pharmaceutical composition for treating cervical cancer, comprising atractylenolide I or a salt thereof, and a P2X7R antagonist, wherein the P2X7R antagonist is BzATP, and a molar ratio of atractylenolide I or the salt thereof to the P2X7R antagonist is (1-10): 1.

2. The pharmaceutical composition according to claim 1, wherein the molar ratio of atractylenolide I or the salt thereof to the P2X7R antagonist is (2-4): 1.

3. The pharmaceutical composition according to claim 1, wherein the cervical cancer is caused by HPV16.

4. A medicament comprising the pharmaceutical composition according to claim 1.

5. A method for treating cervical cancer, comprising administering an effective amount of the medicament according to claim 4 to a subject in need thereof by inhibiting, proliferation of SiHa cells, and clone of SiHa cells.

6. The method according to claim 5, wherein the medicament inhibits the expression of P2X7 receptor protein.

7. The method according to claim 5, wherein the medicament promotes damage of plasma membranes of cervical cancer cells to release LDH.

* * * * *